(12) United States Patent
Schloemer et al.

(10) Patent No.: US 7,307,162 B2
(45) Date of Patent: Dec. 11, 2007

(54) RESOLUTION OF A NARWEDINE AMIDE DERIVATIVE

(75) Inventors: George Schloemer, Longmont, CO (US); Tsung-Yu Hsiao, Kaohsiung County (TW)

(73) Assignee: ScinoPharm Taiwan, Ltd., Taiwan County (TW)

( * ) Notice: Subject to any disclaimer, the term of this patent is extended or adjusted under 35 U.S.C. 154(b) by 124 days.

(21) Appl. No.: 10/951,748

(22) Filed: Sep. 27, 2004

(65) Prior Publication Data

US 2005/0070522 A1 Mar. 31, 2005

Related U.S. Application Data

(60) Provisional application No. 60/506,469, filed on Sep. 26, 2003.

(51) Int. Cl.
*C07D 223/14* (2006.01)
(52) U.S. Cl. ..................................................... 540/521
(58) Field of Classification Search ................. 540/521
See application file for complete search history.

(56) References Cited

U.S. PATENT DOCUMENTS

| 4,290,862 | A | 9/1981 | Vlahov et al. |
| 5,428,159 | A | 6/1995 | Shieh et al. |
| 6,084,094 | A | 7/2000 | Henshilwood et al. |
| 6,369,238 | B1 | 4/2002 | Czollner et al. |
| 6,392,038 | B1 | 5/2002 | Potter et al. |

OTHER PUBLICATIONS

D.H.R. Barton and G.W. Kirby, *Pheonol Oxidation and Biosynthesis Part V, The Synthesis of Galanthamine*, J.Chem. Soc., p. 806 (1962).

T. Kametani et al., *Studies on the Syntheses of Heterocyclic Compounds, Part CCCLXXXVI, Alternative Total Syntheses of Galanthamine and N-Benzylgalanthamine Iodide*, J. Chem. Soc., p. 2602 (1969).

*Primary Examiner*—Bruck Kifle
(74) *Attorney, Agent, or Firm*—Cohen Pontani Lieberman & Pavane LLP

(57) ABSTRACT

The present invention provides for an efficient method of effecting the resolution of a narwedine amide, and the synthesis of galantamine.

12 Claims, No Drawings

RESOLUTION OF A NARWEDINE AMIDE DERIVATIVE

RELATED APPLICATIONS

This application claims priority from U.S. Provisional Patent Application Ser. No. 60/506,469 which was filed on Sep. 26, 2003.

BACKGROUND OF THE INVENTION

1. Field of the Invention

The present invention provides for an efficient method of effecting the resolution of a narwedine amide, and the synthesis of galantamine.

2. Description of the Related Art

Narwedine derivatives have been utilized for the synthesis of (−)galantamine, a natural product derived from Amaryllidaceae species, which has recently been approved as an Alzheimer's drug. Initially this substance was obtained in pure form by extraction from bulbs of Causasian snowdrops but recently (−)galantamine has been shown to be obtained more efficiently by total synthesis. The synthesis of galantamine in either chiral form or achiral form has been the topic of a number of patents and papers.

Galantamine was originally synthesized in optically active form by Barton and Kirby (J. Chem. Soc., 1962(806)) where they demonstrated a resolution by seeding with (+)-galantamine to produce crystals of (−)narwedine which is the precursor to the desired (−)-galantamine by subsequent reduction of the ketone. It was shown that a number of other galantamine derivatives could be used to produce the desired crystallization. In their procedure they employed large amounts of seed crystals. Likewise, U.S. Pat. No. 5,428,159 demonstrates a similar resolution with the use of (−)narwedine as a seed and the use of only 1-2.5% seed equivalence. In either case, an amide had been prepared during the synthesis of the (±) narwedine and this amide was reduced to the free amine prior to the resolution. Therefore, it would be advantageous if an amide precursor could be resolved and the reduction accomplished later in the synthesis.

The synthesis of (±)-galantamine has been previously reported to proceed through the synthesis of bromoamide (I) by the oxidative cyclization of the diphenol (II) (Kametani, et.al., J. Chem. Soc. (C), 2602(1969)). The resolution of this amide has not been reported. One of the apparent difficulties is to obtain a source of seed crystals which contain a similar structure in that this compound is not a natural product. Likewise the change from an amine to an amide would create a different geometry in the molecule and eliminate a source of basic amine useful in the resolution and also create greatly different solubility.

SUMMARY OF THE INVENTION

This invention demonstrates an efficient method of effecting resolution of the narwedine amide derivative (I).

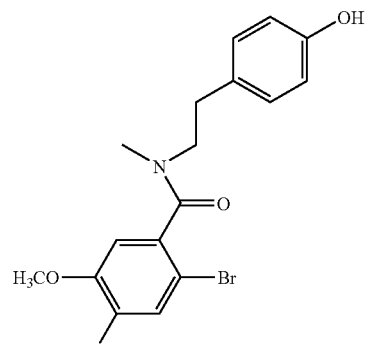

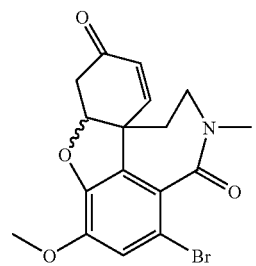

The preparation of the narwedine bromoamide (I) could be accomplished in acceptable yield from the diphenol by oxidation in toluene-water with potassium ferricyanide. It was discovered that this amide derivative is much less soluble in a variety of organic solvents than narwedine itself. However we have found that it can be crystallized with good to excellent optical resolution from a variety of polar solvents. Likewise, we have formed diastereomeric esters of the reduced alcohol form of (I) and we have separated these esters by chromatography. The subsequent hydrolysis of these esters produced the pure chiral alcohols which could be used as seed crystals for the initial studies. Thus, if the racemic bromoamide (I) is dissolved in an organic solvent and an amine base and 0.5-5% of the (+) form of the alcohol III prepared from I is added and the mixture cooled to the point where crystallization occurs, the crystals collected will exhibit significant chiral induction in the form of the (−)enantiomer of (I). In fact, greater than 50% recovery is obtained during this dynamic resolution.

The preferred solvents are alcohols, acetonitrile, ketones and THF, however any solvent that the compound (I) can be crystallized from is viable in this process. The seed crystal can be (−)-galantamine, (−)-bromoamide (I) or the (+)-bromoamide alcohol III. A soluble amine base is employed as a catalyst in order to racemize continually the (+)-bromoamide (I) which remains in solution during the crystallization of the (−)-bromoamide (I). Likewise, a chiral amine base can be employed in place of or in addition to the use of a seed crystal with the desirable effect of increasing the crystallization efficiency. The chiral amine may be preferably α-phenyl ethylamine, cinchonine, cinchonidine, ephredrine, N-methylglucamine. Thus compound (I) together with the amine base is heated in an organic solvent to effect dissolution. The solution is cooled and then maintained at the desired temperature for a period of time to allow slow crystallization. The crystallized solid is then filtered off, washed and dried to produce (−)-bromoamide (I)

substantially enhanced in optical purity. The remaining (±)-bromoamide (I) can be recycled into another optical resolution without loss of material. This provides for a very economical process.

In addition, the present invention further provides for a compound of formula:

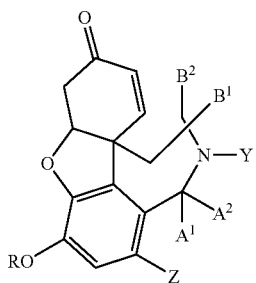

wherein R is selected from the group consisting of H, alkyl, aryl and arylalkyl; A1, A2, are, together, O; B1 and B2 are H; Y is H or Me; and Z is a blocking group. This compound can be resolved by use of a seed crystal or a chiral amine base as discussed above for the resolution of bromoamide (I).

The resolved (−)-bromoamide I can be converted in high yield to (−)galantamine by subsequent reduction of the ketone group to the alcohol (III) of required stereochemistry and finally reduction of the amide and the bromide with lithium aluminum hydride to produce (−)-galantamine. Thus this invention demonstrates an efficient method to produce (−)galantamine by the efficient resolution of the readily available compound I.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

EXAMPLES

One gram of racemic bromoamide (I) is dissolved in 10.5 ml of a 9:1 mixture of acetonitrile and triethyl amine at reflux. A clear solution is formed. The solution is cooled to 80° C. and 10 mg (1%) of optically pure (−)-bromoamide (I) is added to the solution. The solution is then slowly cooled over three hours to 50° C. and held at this temperature for 16 hours with stirring. The product crystallizes to form a suspension. The suspension is cooled to 25° C. and the precipitate is collected by filtration and washed with 4 ml of cold isopropyl alcohol. The cake is dried to yield 705 mg (69.5% yield) of (−)-bromoamide (I) which exhibited an isomer ratio of 99.75 to 0.25 (99.5% ee) by HPLC analysis.

Racemic bromoamide (I) (436 mg) and 5 mg of (−)-galantamine was dissolved in 28 ml of THF and triethyl amine (7:3 ratio) at reflux. A clear solution is formed and 8 ml. of the solution is distilled off. The resulting solution is then cooled to 60° C. and held at this temperature with stirring for 3 hours. The mixture is cooled to 50° C. and held at this temperature overnight. Finally the slurry is cooled to 25° C. and filtered immediately and washed with cold THF to yield 236 mg of dried (−)-bromoamide (I) (53% yield). The product exhibited an isomer ratio of 99.1:0.9 (98.2% ee).

Racemic bromoamide (I) (400 mg) and 4 mg of (+)-bromoamide alcohol (III) are heated to reflux with 14 ml of ethanol and triethyl amine (9:1 ratio) to form a clear solution. The solution is then cooled to 70° C. and at this temperature some precipitate formed. The mixture was further cooled to 50° C. and held at this temperature overnight. Finally the mixture was cooled to room temperature and filtered. (−)-Bromoamide (I) was obtained in 75% yield and exhibited an isomer ratio of 79:21.

Racemic bromoamide (I) (400 mg) and 4 mg of (+)-bromoamide alcohol (III) was dissolved in 30 ml. of a refluxing 9:1 ratio solvent of THF and triethyl amine. A clear solution is formed. The solution is distilled to remove 10 ml of solvent and then cooled to 50° C. and held at this temperature with stirring for 18 hours. The precipitated solid was filtered off at room temperature and washed with 4 ml of THF. The product was dried to produce 245 mg (61% yield) of (−)-bromoamide (I) which exhibited an isomer ratio of 92:8 (84% ee) by HPLC analysis.

Racemic bromoamide (I) (400 mg) and 4 mg of (+)-bromoamide alcohol (III) was dissolved in 10.5 ml of acetone and triethyl amine (9:1) at reflux to form a clear solution. The solution was cooled to 40° C. over 3 hours and held at this temperature for 16 hours to form a suspension of white solid. The mixture was cooled to 25° C. and filtered. The cake was washed with 4 ml of cold isopropyl alcohol and dried to yield 161 mg of (−)-bromoamide (I) with an isomer ratio of 98:2 (96% ee).

Racemic bromoamide (1) (300 mg) and 20 mg of (−)-α-methylphenylethyl amine was heated at 80° C. in 4 ml of acetonitrile until complete dissolution. The solution was cooled to 70° C. and a white precipitate formed. No seed crystals were added. The solid was collected by filtration and exhibited an isomer ratio of 24:76 of (+)-bromoamide (I).

The invention is not limited by the embodiments described above which are presented as examples only but can be modified in various ways within the scope of protection defined by the appended patent claims. The references cited herein are incorporated by reference in their entirety.

What is claimed is:
1. A method of producing a (−) enantiomer of the compound of formula (I) from racemic bromoamide

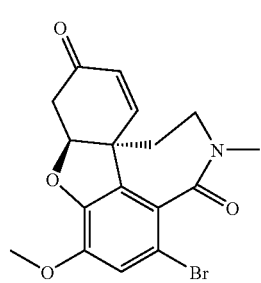

by the steps of (a) dissolving the racemic bromoamide in an organic solvent containing a soluble base to form a mixed solution, (b) seeding the mixed solution with a seed crystal of an optically active material, and (c) crystallizing the seeded mixed solution to produce (−) bromoamide (I) with substantially enhanced optical purity.

2. The method of claim 1 in which the organic solvent is selected from the group consisting of acetonitrile, alcohol, acetone and THF.

3. The method of claim 1 in which the soluble base is an amine.

4. The method of claim 3 wherein the amine is trialkyl amine.

5. The method in claim 1 in which the seed crystal is selected from the group consisting of (+) bromoamide alcohol (III)

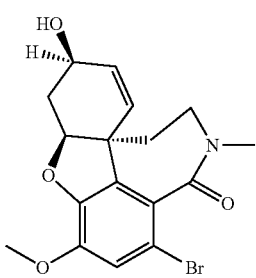

,(+) galantamine and (−) bromoamide (I).

6. A method of producing a (−) enantiomer of the compound of formula (I) from racemic bromoamide

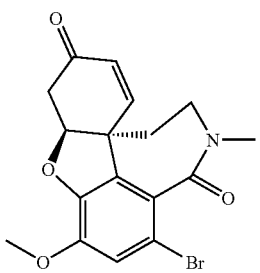

by the steps of (a) dissolving the racemic bromoamide in an organic solvent containing a soluble chiral amine base to form a mixed solution, and (b) crystallizing the mixed solution to produce (−) bromoamide (I) with substantially enhanced optical purity.

7. The method of claim 6, wherein the chiral base amine is selected from the group consisting of α-phenyl ethylamine, cinchonine, cinchonidine, ephredrine, and N-methylglucamine.

8. The method of claim 6 in which a seed crystal of an optically active material is added to the mixed solution to crystallize the (−) bromoamide (I).

9. The method of producing (−)-galantamine comprising the steps of claim 1, converting the (−) bromoamide (I) to the alcohol, and reducing the alcohol to (−)-galantamine.

10. The method of producing (−)-galantamine comprising the steps of claim 6, converting the (−) bromoamide (I) to the alcohol, and reducing the alcohol to (−)-galantamine.

11. The method of producing a (−) enantiomer from the racemic compound

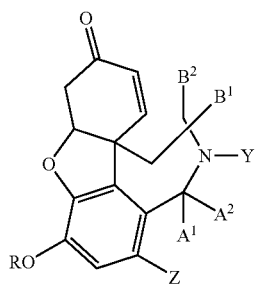

wherein R is selected from the group consisting of H, alkyl, aryl and arylalkyl; A1 and A2 are, together, 0; B1 and B2 are H; Y is H or Me; and Z is a blocking group; by the steps of (a) dissolving the racemic compound in an organic solvent containing a soluble base to form a mixed solution, (b) seeding the mixed solution with a seed crystal of an optically active material, and (c) crystallizing the seeded mixed solution to produce the (−) enantiomer with substantially enhanced optical purity.

12. The method of producing a (−) enantiomer from racemic compound of

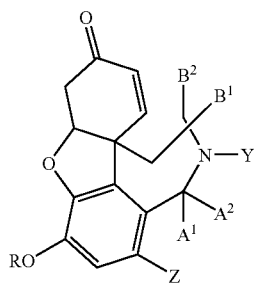

wherein R is selected from the group consisting of H, alkyl, aryl and arylalkyl; A1 and A2 are, together, 0; B1 and B2 are H; Y is H or Me; and Z is a blocking group;

by the steps of (a) dissolving the racemic compound in an organic solvent containing a soluble chiral amine base to form a mixed solution, and (b) crystallizing the mixed solution to produce the (−) enantiomer with substantially enhanced optical purity.

* * * * *

UNITED STATES PATENT AND TRADEMARK OFFICE
CERTIFICATE OF CORRECTION

PATENT NO. : 7,307,162 B2
APPLICATION NO. : 10/951748
DATED : December 11, 2007
INVENTOR(S) : George Schloemer and Tsung-Yu Hsiao It is certified that error appears in the above-identified patent and that said Letters Patent is hereby corrected as shown below:

Column 5, line 27, the text, ", (+) galantamine and (–) bromoamide (1)" should be changed to
-- , (–) galantamine and (–) bromoamide (1). --

Signed and Sealed this
Ninth Day of August, 2011

David J. Kappos
*Director of the United States Patent and Trademark Office*